United States Patent
Krahn

[11] Patent Number: 6,156,043
[45] Date of Patent: Dec. 5, 2000

[54] SOFT TISSUE MORSELLATOR

[76] Inventor: Henry P. Krahn, 1402 Medical Arts Building, 233 Kennedy Street, Winnipeg, Canada, R3C 3J5

[21] Appl. No.: 09/283,524

[22] Filed: Apr. 1, 1999

Related U.S. Application Data
[60] Provisional application No. 60/086,637, May 26, 1998.

[51] Int. Cl.[7] .................................................. A61B 17/24
[52] U.S. Cl. .......................... 606/110; 606/167; 606/170
[58] Field of Search .................................. 606/110, 113, 606/114, 115, 127, 128, 79, 170, 171, 167

[56] References Cited

U.S. PATENT DOCUMENTS

| | | | |
|---|---|---|---|
| 3,181,533 | 5/1965 | Heath | 606/113 |
| 3,828,790 | 8/1974 | Curtiss et al. | 606/113 |
| 4,768,505 | 9/1988 | Okada et al. | 606/127 |
| 4,927,427 | 5/1990 | Kriauciunas et al. | 606/128 |
| 5,057,114 | 10/1991 | Wittich et al. | 606/127 |
| 5,059,199 | 10/1991 | Okada et al. | 606/127 |
| 5,336,238 | 8/1994 | Holmes et al. | |
| 5,397,320 | 3/1995 | Essig et al. | 606/127 |
| 5,658,296 | 8/1997 | Bates et al. | 606/127 |
| 5,722,988 | 3/1998 | Weisshaupt | |
| 5,961,526 | 10/1999 | Chu et al. | 606/113 |

*Primary Examiner*—Gene Mancene
*Assistant Examiner*—Eduardo C. Robert
*Attorney, Agent, or Firm*—Olson & Hierl, Ltd.

[57] ABSTRACT

A soft tissue morsellator for reducing the size of tissue fragments generated during surgery is provided. The morsellator includes a shaft movable within a housing for positioning a receptacle from a retracted position, wherein the receptacle is nested within a distal end of the housing, to an extended position, wherein the receptacle is deployed outside the housing. The shaft is activated by an actuator attached thereto. The receptacle is configured from a pair or plurality of wire hoops having a cutting edge along a portion of each. The soft tissue morsellator is provided with an irrigation liquid drain for removal of reduced tissue fragments and may include a hollow channel in the housing for receiving an endoscope therein to aid in the location of larger tissue fragments.

19 Claims, 7 Drawing Sheets

SOFT TISSUE MORSELLATOR

CROSS-REFERENCE TO RELATED APPLICATION

This application claims the benefit of U.S. Provisional Application No. 60/086,637, filed on May 26, 1998.

TECHNICAL FIELD

The invention relates generally to the field of medical devices. More specifically, the present invention relates to a soft tissue morsellator.

BACKGROUND OF THE INVENTION

During the course of medical procedures, i.e. prostate surgery and the like, large fragments of tissue are often cut that are too bulky and difficult to remove with standard techniques such as irrigation and curettage. Therefore, a demand exists for a hand-held device to reduce the size of the tissue and facilitate removal of the tissue material.

SUMMARY OF THE INVENTION

The present invention includes a soft tissue morsellator generally having a cutting device which may be operated at the end of an elongated surgical instrument to reduce the size of and clear away tissue fragments throughout the course of a surgical procedure while still providing for minimal invasiveness and easy disassembly for effective sterilization.

A soft tissue morsellator embodying the present invention has an actuator connected to a shaft or the like which is movable through a tubular housing and is connected to a basket or receptacle at the opposite end.

The basket or receptacle functions as the cutting device and consists of a number of wire loops or hoops with a cutting edge along at least a portion of each, where preferably the cutting edge is formed along the inner surface. This cutting device may be withdrawn into the tubular housing or expanded therefrom by action of the actuator on the shaft connected to the basket or receptacle to present a cutting configuration thereof.

Additionally, an irrigation drain can be provided at the end of the tubular housing near the actuator. Such drain may be connected to an evacuation system to aid in the removal of the tissue fragments generated by the morsellator.

As the device is manually operated, there is greater control and sensitivity, thereby greatly reducing the risk of damage to surrounding tissues.

Preferably, the soft tissue morsellator includes a channel for an endoscope mounted onto the housing so that the instrument may be guided to the tissue fragments thereby.

BRIEF DESCRIPTION OF THE DRAWINGS

In the accompanying drawings forming part of the specification, and in which like numerals are used to designate like parts throughout the same.

DESCRIPTION OF PREFERRED EMBODIMENTS

Figure 1:
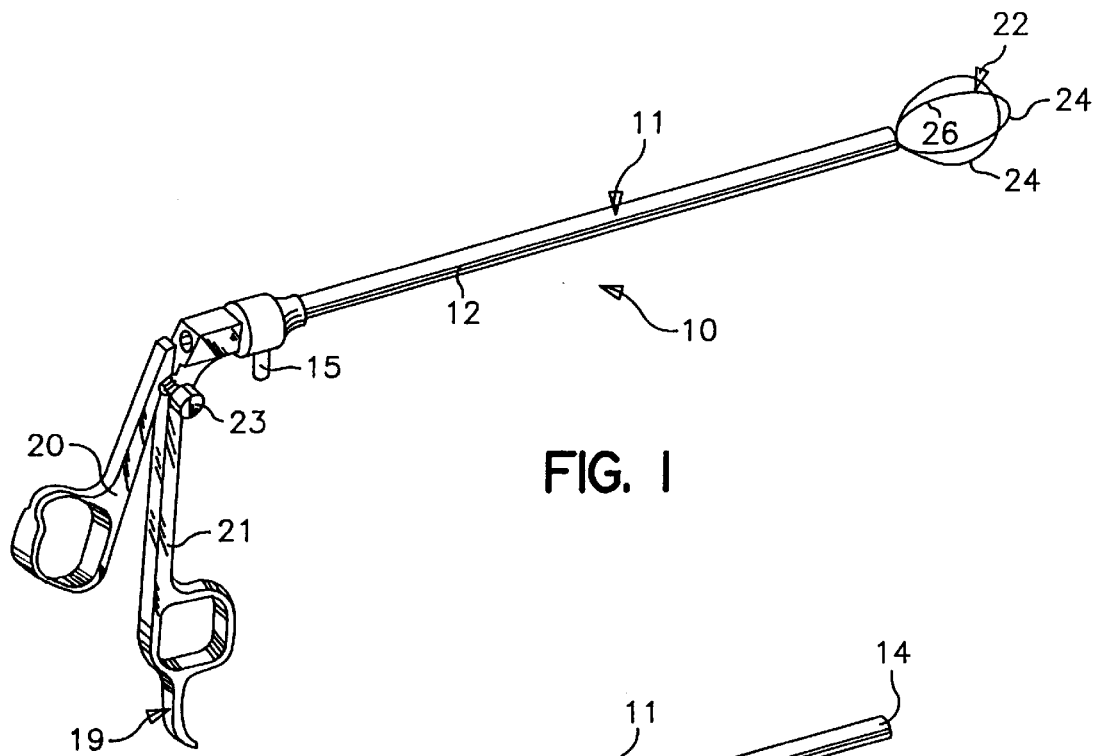
FIG. 1 is a perspective view of the soft tissue morsellator embodying the present invention in the extended position.

The invention disclosed herein is, of course, susceptible of embodiment in many different forms. Shown in the drawings and described hereinbelow in detail are certain preferred embodiments of the present invention. It is to be understood, however, that the present disclosure is an exemplification of the principles of this invention and does not limit the invention to the illustrated embodiments.

Figure 2:
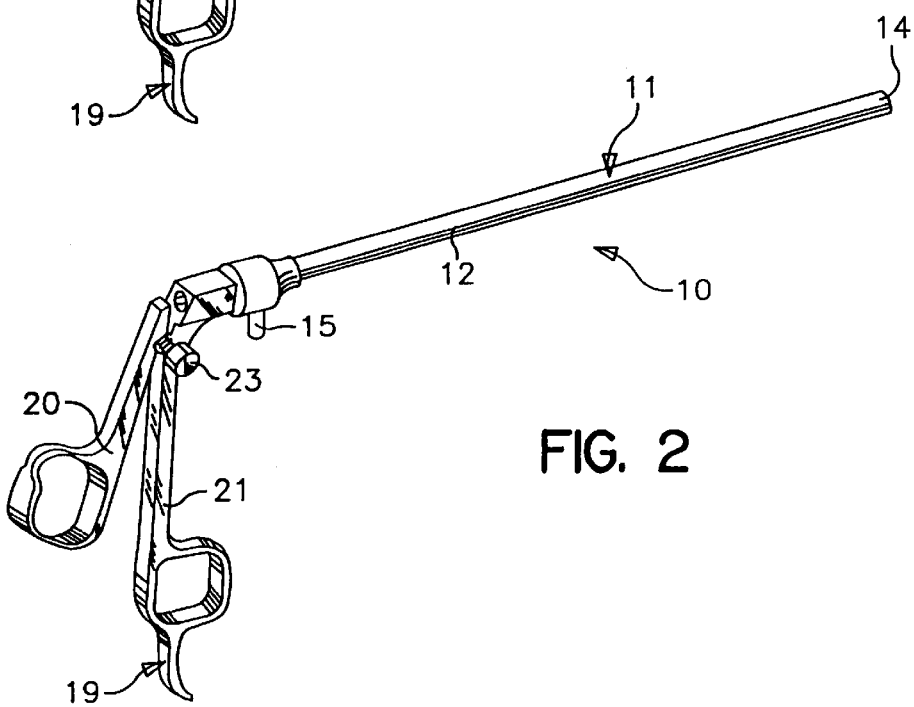
FIG. 2 is a perspective view of the soft tissue morsellator of FIG. 1 in the retracted position.
Figure 3:
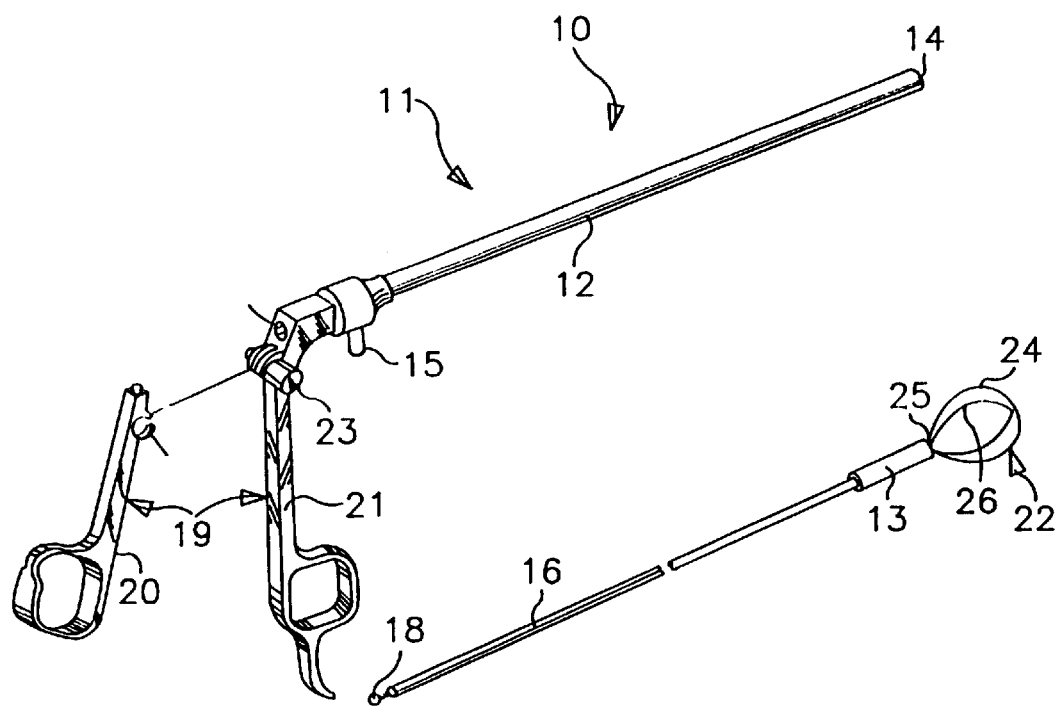
FIG. 3 is a perspective view of the soft tissue morsellator of FIG. 2 in disassembled condition.

Referring to the drawings, a soft tissue morsellator 10 embodying the present invention is shown in FIGS. 1–3. Soft tissue morsellator 10 includes longitudinally collapsible receptacle 22 defined by a plurality of flexible loops 24 which have a cutting edge 26 along at least a portion of each loop 24, preferably along the inner surface of the loop 24. Affixed to the receptacle 22 is a handle 11 with an actuator device 19 operably associated with the receptacle 22 for manipulating the receptacle 22 between a collapsed configuration and an expanded configuration.

Handle 11 includes a tubular housing 12, arranged to be inserted into a body orifice, i.e. the urethra, having an open distal end 14 for the housing, and a shaft 16 within the tubular housing 12 (FIG. 3) and axially movable therein. An optional hollow channel can be provided in tubular housing 12 for receiving therein an endoscope or the like viewing system. Handle 11 also includes an irrigation liquid drain 15, connectable to an evacuation system for removal of liquid and/or material which has been comminuted by action of the loops 24.

Shaft 16 has a cylindrical guide element 13 near distal end 25 of shaft 16 and a proximal end 18 operably connected to the actuator device 19 for imparting axial reciprocal movement to the shaft 16 and positioning basket or receptacle 22 from a collapsed configuration within the open distal end portion 14 of the tubular housing 12, shown in FIG. 2, to an expanded configuration shown in FIG. 1. When expanded, the basket or receptacle 22 is located outside the tubular housing 12. In another embodiment, the shaft 16 may be rotatably mounted within the tubular housing 12. In yet another embodiment, shown in FIG. 4 and discussed hereinbelow, a plurality of rods or wires can be utilized in lieu of shaft 16.

As shown in FIGS. 1–4, actuator 19 is constituted by a pair of pivotally connected handle elements 20 and 21 connected by fastener 23. One of the elements 20 is mounted to the tubular housing 12, and the other one of the elements 21 is connected to the shaft 16.

Basket or receptacle 22 is a longitudinally collapsible, substantially globular element mounted to one end of the shaft 16 and is adapted for nesting within a distal end portion 14 of the housing 12 when collapsed, and for extending beyond the open distal end 14 of the housing 12 when expanded. Basket or receptacle 22 is defined by a pair or plurality of flexible hoops 24 fixed to the shaft 16 and having a cutting edge 26 along a portion of the periphery thereof, preferably along a portion of the inner surface thereof.

Figure 9:
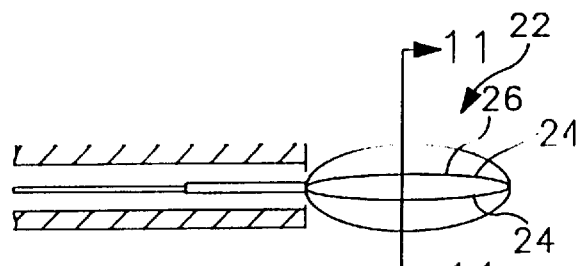
FIG. 9 an is enlarged partial cross-sectional side view of the collapsible receptacle of FIGS. 1–4.

As can be seen in FIG. 1 and 9, the flexible hoops 24 are arranged in pairs on opposing sides of the shaft 16 and may be interconnected at this point, or in another embodiment, interconnected at a location away from the shaft 16. The hoops 24 are designed to have a memory such that they will bow outwardly relative to the interconnected ends of the flexible hoops 24. The flexible hoops 24 form a basket or receptacle 22 for grasping tissue fragments as will be discussed in greater detail hereinbelow.

The inner surfaces of the flexible hoops 24 are arranged to face one another with a cutting edge 26 along a portion thereof.

Figure 4:
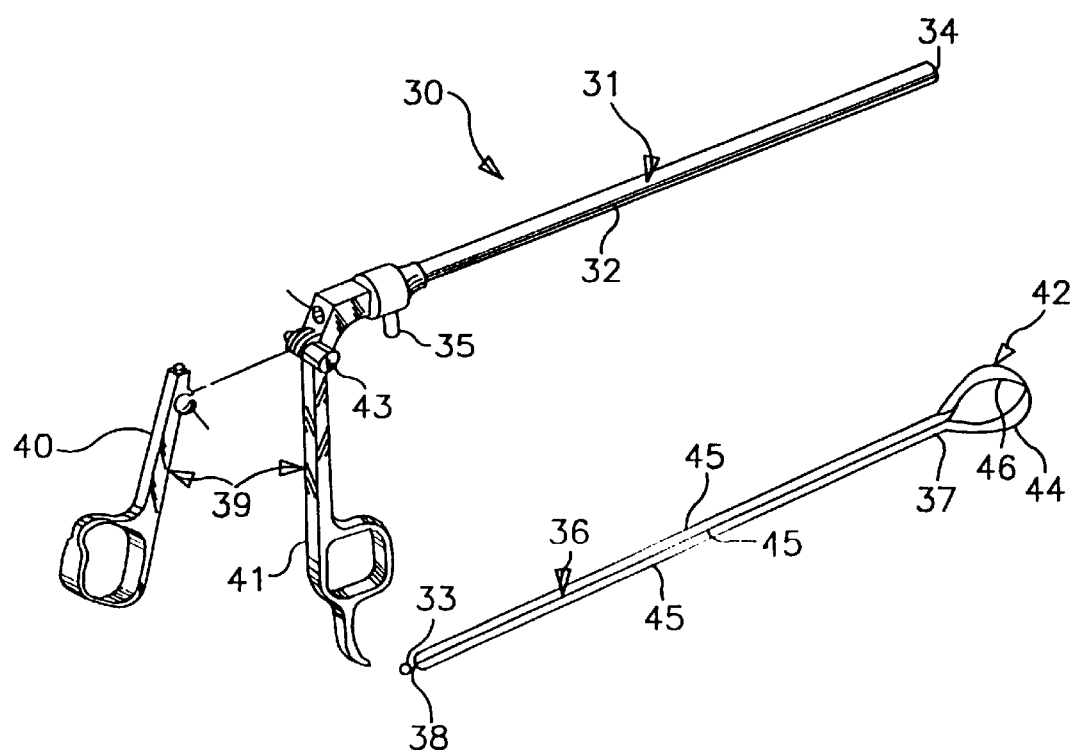
FIG. 4 shows a second embodiment of the soft tissue morsellator of FIG. 1 in disassembled condition.

As shown in FIG. 4 in an alternate embodiment, soft tissue morsellator 30 includes longitudinally collapsible cage 42 constituted by a plurality of flexible hoops 44 which have a cutting edge 46 along at least a portion of each hoop 44, preferably along the inner surface. Affixed to cage 42 is support element 31 with an actuator device 39 operably associated with cage 42 for maneuvering cage 42 between a collapsed configuration and an expanded configuration.

Support element 31 includes tubular housing 32 designed to be inserted into a body orifice, i.e. the urethra, having an open distal end 34 for the housing, and copula 36 within the tubular housing 32 and axially moveable therein. As with previous embodiments, an optional hollow channel can be provided in tubular housing 32 for receiving therein an endoscope or the like viewing system. Support element 31 also includes an irrigation liquid drain 35, connectable to an evacuation system for removal of liquid and/or material which has been minified by action of the hoops 44.

Copula 36 includes a plurality of wires 45 connected at a distal end 37 of wires 45 to cage 42, and connected at a proximal end 38 of wires 45 to ball 33. Ball 33 is operably connected to actuator 39 for imparting axial reciprocal movement to wires 45 and positioning cage 42 from a collapsed configuration within the open distal end portion 34 of the tubular housing 32, shown in FIG. 2, to an expanded configuration, shown in FIG. 1. In yet another embodiment, wires 45 may be replaced with rods.

Actuator 39 is constituted by a pair of pivotally connected handle elements 40 and 41 by a threaded bolt 43. One of the elements 40 is mounted to the tubular housing 32, and the other one of the elements is connected to ball 33.

Cage 42 is a longitudinally collapsible, substantially globular element mounted to the distal end 37 of wires 45 and is adapted for folding within a distal end portion 34 of the housing 32 when collapsed, and for extending beyond the open distal end 34 of the housing 32 when expanded. Cage 42 is defined by at least a pair of flexible loops 44 fixed to the distal end 37 of wires 45 having the cutting edge 46 formed along at least a portion of an inner surface thereof.

The hoops 44 are arranged in pairs, each pair having two orthogonal hoops 44. While a plurality of hoops 44 are preferred, a cage 42 defined by at least one pair of hoops is contemplated. The hoops 44 are designed to have a memory such that they will bow outwardly relative to the interconnected ends of the flexible hoops 44. The flexible hoops 44 form a cage 42 for grasping tissue fragments as will be discussed in greater detail hereinbelow.

Referring to the drawings, a soft tissue morsellator 110 embodying the present invention is shown in FIGS. 5–8. Correspondingly, where appropriate, the last two digits in the 100 series of numerals depicted in FIGS. 5–8 are connected to elements which have the same function and/or structure as those described with regard to FIGS. 1–4. Soft tissue morsellator 110 includes longitudinally collapsible receptacle 122 defined by a plurality of flexible wires, preferably formed of nitinol, or loops 124, have a cutting edge 126 formed along at least a portion of each loop 124. Additionally, it is contemplated that this embodiment include a longitudinally collapsible cage 142 defined by a plurality of flexible wires 145 having cutting edge 146 formed along at least a portion thereof. Affixed to the receptacle 122 or cage 142 is a handle 111 with an actuator device 119 operably associated with the receptacle 122 or cage 142 for manipulating the receptacle 122 or cage 142 between a collapsed configuration and an extended configuration.

In the depicted embodiment, receptacle 122 or cage 142 has an elliptical, football-like shape when viewed from the side. In the depicted embodiment, loop 124 or wires 145, preferably comprised of nitinol wires though other wires are contemplated, are interconnected at a distal end 147 of said receptacle 122 or cage 142, preferably by welding.

Handle 111 includes a tubular housing 112, arranged to be inserted into a body orifice, i.e. the urethra, having an open distal end 114 for the housing, a shaft 116 within the tubular housing 112 (FIG. 7) and axially movable therein. An optional hollow channel can be provided in tubular housing 112 for receiving therein an endoscope viewing system or the like. Handle 111 also includes an irrigation liquid drain 115, connectable to an evacuation system for removal of liquid and/or material which has been comminuted by action of the loops 124 or wires 145.

Shaft 116 has a cylindrical guide element 113 near distal end 125 of shaft 116, and a proximal end 118 operably connected to the actuator device 119 for imparting axial reciprocal movement to the shaft 116. Imparting axial movement to the shaft 116 positions receptacle 122 or cage 142 from a collapsed configuration within the open distal end portion 114 of the tubular housing 112, shown in FIG. 6, to an extended configuration shown in FIG. 5. When extended, the receptacle 122 or cage 142 is located outside the tubular housing 112. In another embodiment, the shaft 116 may be rotatably mounted within the tubular housing 112. In yet another embodiment, shown in FIG. 8 and discussed hereinbelow, a plurality of rods or wires can be utilized in lieu of shaft 116.

Figure 5:
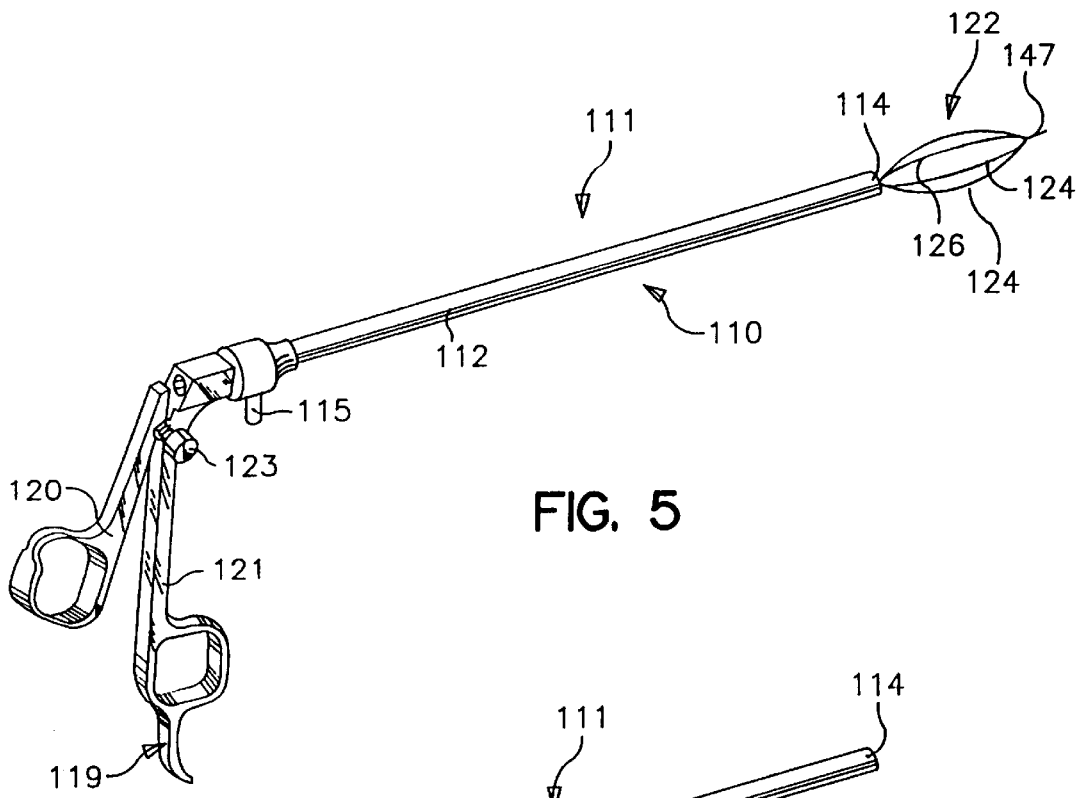
FIG. 5 is a perspective view of a third embodiment of the soft tissue morsellator in the extended position.
Figure 6:
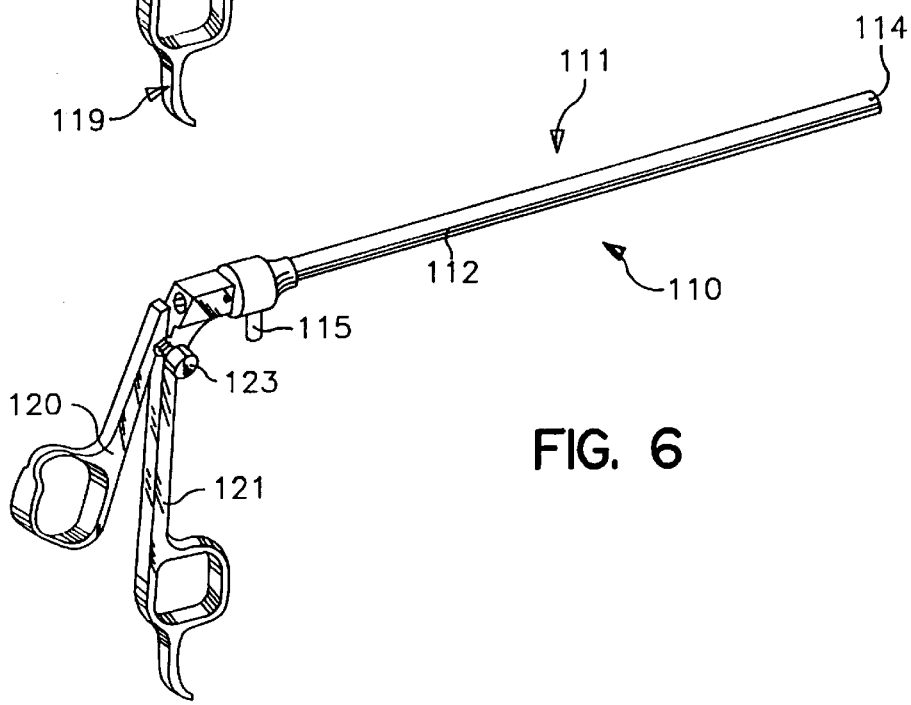
FIG. 6 is a perspective view of the soft tissue morsellator of FIG. 5 in the retracted position.
Figure 7:
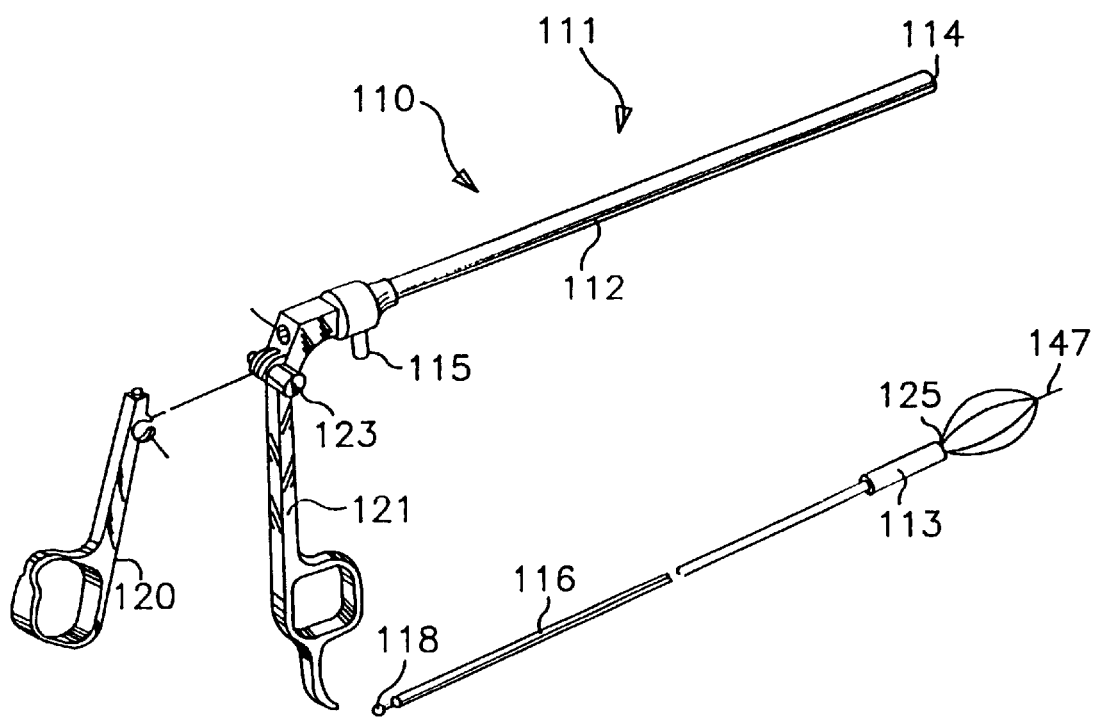
FIG. 7 is a perspective view of the soft tissue morsellator of FIG. 5 in a disassembled condition.

As shown in FIGS. 5–7, actuator 119 is constituted by a pair of pivotally connected handle elements 120 and 121 connected by fastener 123. One of the elements 120 is mounted to the tubular housing 112, and the other one of the elements 121 is connected to the shaft 116.

Receptacle 122 or cage 142 is a longitudinally collapsible, substantially elliptically shaped element mounted to one end of the shaft 116 and is adapted for nesting within the distal end portion 114 of the housing 112 when collapsed, and for extending beyond the open distal end 114 of the housing 112 when expanded. Receptacle 122 is defined by a pair or plurality of flexible hoops 124, preferably having a cutting edge formed along a periphery thereof, or wires 145 of a suitable small diameter, preferably of nitinol and fixed to the shaft 116 and having a cutting edge 126 along a portion of the periphery thereof.

Figure 10:
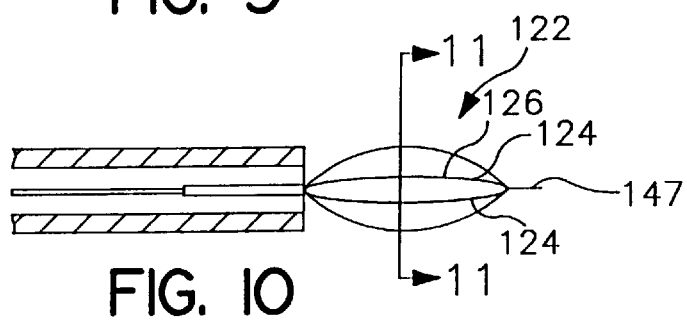
FIG. 10 is an enlarged partial cross-sectional side view of the collapsible cage of FIGS. 5–8.

As can be seen in FIG. 5 and 10, the flexible hoops 124 or wires 145 are arranged in pairs on opposing sides of the shaft 116 and are interconnected at a location away from the shaft 116 at a distal end 147. Preferably hoops 124 or wires 145 are welded. The hoops 124 or wires 145 are designed to have a memory such that they will bow outwardly relative to the distal end 147, forming a receptacle 122 or cage 142 for grasping tissue fragments as will be discussed in greater detail hereinbelow.

The inner surfaces of the flexible hoops 124 are arranged to face one another with a cutting edge 126 formed along a portion thereof. In the preferred embodiment, hoops 124 or wires 145 are formed with a cutting edge 126 along at least a portion of an inner surface 148, all facing towards a center of the receptacle 122 or cage 142.

Figure 8:
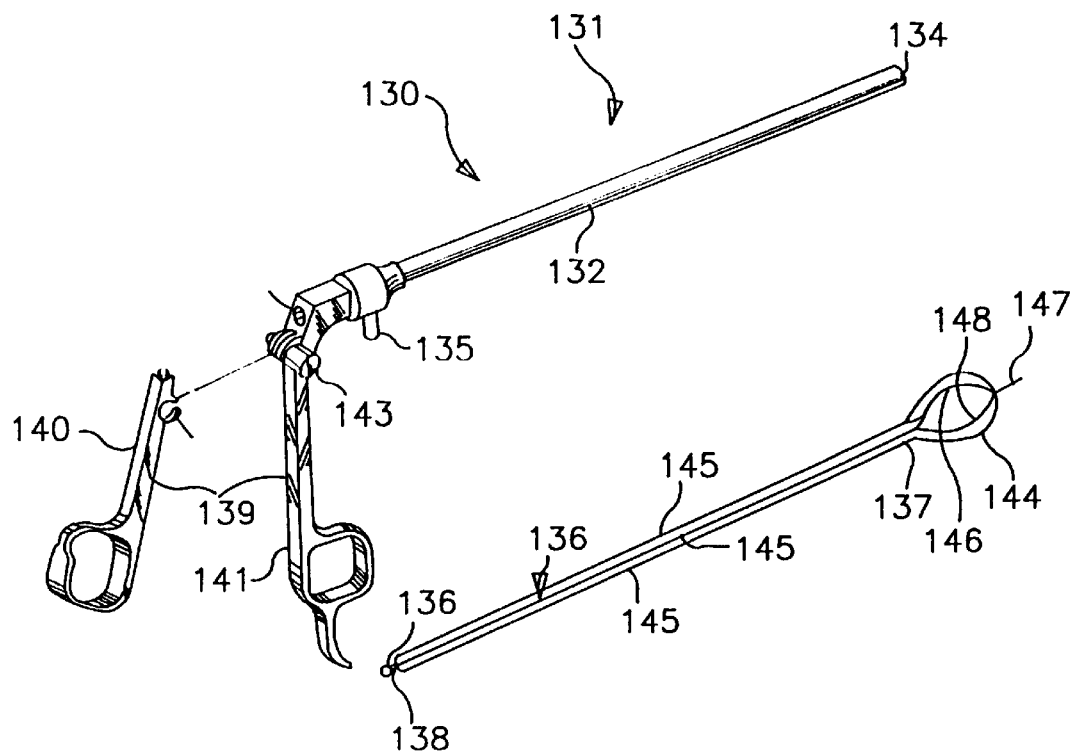
FIG. 8 shows a fourth embodiment of the soft tissue morsellator in a disassembled condition.

As shown in FIG. 8, yet another embodiment of the present invention is depicted. Soft tissue morsellator 130 includes longitudinally collapsible cage 142 constituted by a plurality of flexible hoops 144 which have a cutting edge 146 along at least a portion of inner surface 148. Affixed to cage 142 is support element 131 with an actuator device 139 operably associated with cage 142 for maneuvering cage 142 between a collapsed configuration and an extended configuration.

Support element 131 includes tubular housing 132 designed to be inserted into a body orifice, i.e. the urethra, an open distal end 134 for the housing, and copula 136 within the tubular housing 1:32 and axially moveable therein. As with previous embodiments, an optional hollow channel can be provided in tubular housing 132 for receiving therein an endoscope viewing system or the like. Support element 131 also includes an irrigation liquid drain 135, connectable to an evacuation system for removal of liquid and/or material which has been minified by action of the hoops 144 or wires 145.

Copula 136 includes the plurality of wires 145 connected at distal end 137 to the hoops 144 of cage 142, and connected at proximal end 138 to ball 133. Alternatively, wires 145 and hoops 144 of cage 142 and copula 136 could be integral therewith. Ball 133 is operably connected to actuator 139 for imparting axial reciprocal movement to wires 145. Such axial reciprocal movement positions cage 142 from a collapsed configuration within the open distal end portion 134 of the tubular housing 132, shown in FIG. 2, to an expanded extended configuration, shown in FIG. 7. In an yet another embodiment, wires 145, preferably formed of nitinol wire, may be replaced with rods.

Actuator 139 is constituted by a pair of pivotally connected handle elements 140 and 141 by a threaded bolt 143. One of the elements 140 is mounted to the tubular housing 132, and the other one of the elements is connected to ball 133.

Cage 142 is a longitudinally collapsible, substantially globular element mounted to the distal end 137 of wires 145 or integral therewith and is adapted for folding within a distal end portion 134 of the housing 132 when collapsed, and for extending beyond the open distal end 134 of the housing 132 when expanded. Cage 142 is defined by a pair of plurality of flexible wires 145 or loops 144 fixed to distal end 137 or integral therewith, said loops 144 having a cutting edge 146 formed along at least a portion of an inner surface 148 of each.

Figure 11A:
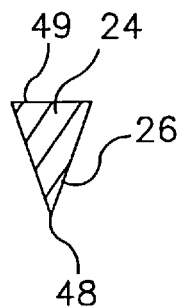
FIGS. 11A–11F are a cross-sectional view of one of the loops or wires taken substantially along line 11—11 of FIGS. 9 and 10.
Figure 11B:
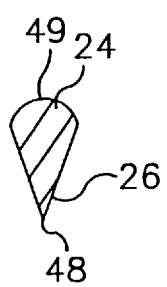
Figure 11C:
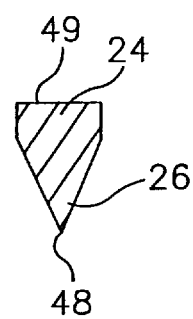
Figure 11D:
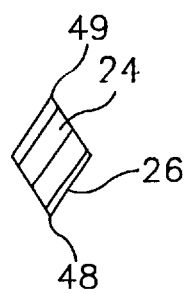
Figure 11E:
Figure 11F:

Turning now to FIGS. 11A–11D taken substantially along line 11—11 of FIGS. 9 and 10, various embodiments of hoops 24 and 44 are depicted in on cross-section. As shown, it is contemplated that hoops 24 and 44, and wires 145, are formed with outer edge 49 opposite inner edge 48. In one embodiment cutting edge 26 is formed along a portion of hoops 24 and 44 along a portion of inner edge 148. Moreover, outer edge 49 is formed having a plurality of shapes only some of which are depicted. It is contemplated that hoops 24 and 44 have a flat outer edge (FIG. 11A), a rounded outer edge (FIG. 11B), a squared off outer edge (FIG. 11C) or even a pointed outer edge (FIG. 11D) among others. FIG. 11E depicts a wire 50 of sufficiently small diameter to cut soft tissue without using a sharp inner surface. FIG. 11F depicts a wire 52 of small diameter with a sharp inner surface.

In use, referring again to FIGS. 1–4, the soft tissue morsellator 10 with the shaft 16 and the receptacle 22 in the retracted position is inserted into a body orifice. The user directs the soft tissue morsellator 10 to the desired location, that is, the location of the tissue fragment, optionally using an endoscope. When the soft tissue morsellator 10 is in the desired location, the shaft 16 and receptacle 22 are slid into the extended position via the actuator 19. As a result of this action, flexible hoops 24 extend out from the open distal end 14 of tubular housing 12 and form basket 22. Basket 22 is then manipulated such that the tissue fragment is entrapped by flexible hoops 24 and is located within basket 22.

The user then squeezes handle elements. 20 and 21 of the soft tissue morsellator 10 which slides the shaft 16 and the basket 22 from the extended position to the retracted position. As this occurs, the flexible loops 24 are withdrawn into the tubular housing 12 at the open distal end 14. Consequently, the overall size of basket 22 is reduced, causing the cutting edge 26 on the inner surfaces of flexible loops 24 to contact the entrapped tissue fragment. As the basket 22 is retracted further, the flexible hoops 24 cut through the tissue fragment, resulting in several smaller tissue fragments. This process can be repeated as needed until the tissue fragments are small enough to be easily removed via irrigation and liquid drain 15, or other suitable method.

The third and fourth embodiments of the soft tissue morsellator 110 are used in the same fashion as the first and second embodiments. The soft tissue morsellator 110 is placed in position at the desired location. Manipulating actuator 119 causes the shaft 116 and receptacle 122 or cage 142 to slide into the extended position. The flexible wires 145 extend out of the open distal end 114 of the housing 112, forming basket 122 or cage 142, so that the tissue fragments are entrapped.

Squeezing handle elements 120 and 121 slides the shaft 116 and receptacle 122 or cage 142 to the retracted position. The overall size of basket 122 or cage 142 is reduced, causing the cutting edge 126 on the inner surface 148 of wires 145 to contact the entrapped tissue fragments as receptacle 122 or cage 142 is retracted further, the wires 145 cut through the tissue fragment, thereby resulting in several small tissue fragments.

It is of note that the number of sub-fragments produced from the initial tissue fragment is directly proportional to the number of flexible loops 24. However, fewer flexible loops 24 will enable larger fragments to pass between the loops into the basket. As is apparent, any number of flexible loops 24 may be used provided that the remaining receptacle or basket 22 can admit a tissue fragment therein.

The foregoing specification and drawings are intended as illustrative, and are not to be taken as limiting. Still other variations, modifications and rearrangements of parts are possible without departing from the spirit and scope of the present invention.

I claim:

1. A soft tissue morsellator which comprises:

a tubular housing having an open distal end;

a shaft within the tubular housing including a ball and axially movable therein;

a longitudinally collapsible, substantially globular basket mounted to one end of the shaft and adapted for nesting within a distal end portion of the housing when collapsed and extending beyond the open distal end of the housing when expanded; and an actuator operably connected to the ball of the shaft for imparting axial reciprocal movement to the shaft and positioning the basket from a collapsed configuration within the distal end portion of the housing to an expanded configuration outside the housing;

said basket being defined by a plurality of flexible hoops fixed to the shaft and having a cutting edge along at least a portion of the periphery thereof adapted to contact and cut the soft tissue.

2. The soft tissue morsellator according to claim 1 wherein said hoops are interconnected at a location away from the shaft.

3. The soft tissue morsellator according to claim 1 wherein said shaft is rotatably mounted within the tubular housing.

4. The soft tissue morsellator according to claim 1 wherein said basket is defined by a pair of hoops.

5. The soft tissue morsellator according to claim 1 wherein the actuator is a handle assembly comprising a pair of pivotally connected handle elements, one of the elements being mounted to the tubular housing and the other of the elements being connected to the shaft.

6. A soft tissue morsellator which comprises:

a longitudinally collapsible cage defined by a plurality of flexible wires interconnected at a proximal end to a ball; and an actuator device operably connected to the ball and associated with the longitudinally collapsible cage for manipulation thereof between a collapsed configuration and an extended configuration.

7. The soft tissue morsellator according to claim 6 wherein said actuator device includes a handle affixed to the longitudinally collapsible cage.

8. The soft tissue morsellator according to claim 7 wherein said flexible wires are interconnected at a distal end of the collapsible cage.

9. The soft tissue morsellator according to claim 8 wherein said flexible wires are welded at the distal end of the collapsible cage.

10. A soft tissue morsellator which comprises:

a longitudinally collapsible receptacle defined by a plurality of flexible loops having an outer edge and a cutting edge formed along at least a portion of the inner surface of each loop and located opposite the outer edge for contacting and cutting the soft tissue; and an actuator operably associated with the receptacle for manipulating the receptacle between a collapsed and an expanded configuration.

11. The soft tissue morsellator according to claim 10 wherein said actuator includes a shaft.

12. The soft tissue morsellator according to claim 11 wherein said loops are interconnected at a location away from the shaft.

13. The soft tissue morsellator according to claim 11 wherein said shaft is rotatably mounted within a tubular housing.

14. The soft tissue morsellator according to claim 11 wherein said flexible loops are nitinol wire.

15. The soft tissue morsellator according to claim 11 wherein the actuator is a handle assembly comprising a pair of pivotally connected handle elements, one of the elements being mounted to a tubular housing and the other of the elements being connected to the shaft.

16. The soft tissue morsellator according to claim 10 wherein said receptacle is defined by at least one pair of flexible loops.

17. A soft tissue morsellator which comprises:

a tubular housing having an open distal end;

a longitudinally collapsible, substantially globular cage movably disposed within the housing, which is adapted for nesting within a distal end portion of the housing when collapsed and extending beyond the open distal end of the housing when expanded; and an actuator operably connected to a proximal end of the cage for imparting axial reciprocal movement thereto, enabling the cage to expand from a collapsed configuration within the distal end portion of the housing to an extended configuration outside the housing;

said cage being defined by a plurality of flexible hoops all having a cutting edge formed along at least a portion of the inner surface thereof and facing towards the center of the cage, the cutting edge of the hoops being adapted to contact and cut the soft tissue.

18. The soft tissue morsellator according to claim 17 wherein said actuator includes a shaft moveable mounted within the tubular housing.

19. The soft tissue morsellator according to claim 17 wherein said plurality of flexible hoops further define a shaft moveable mounted within the tubular housing.

* * * * *